(12) United States Patent
Ohtake et al.

(10) Patent No.: US 10,262,417 B2
(45) Date of Patent: Apr. 16, 2019

(54) TOOTH AXIS ESTIMATION PROGRAM, TOOTH AXIS ESTIMATION DEVICE AND METHOD OF THE SAME, TOOTH PROFILE DATA CREATION PROGRAM, TOOTH PROFILE DATA CREATION DEVICE AND METHOD OF THE SAME

(71) Applicant: FUJITSU LIMITED, Kawasaki-shi, Kanagawa (JP)

(72) Inventors: Ryosuke Ohtake, Atsugi (JP); Katsumi Umekawa, Yokohama (JP); Tatsukiyo Ishimura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 141 days.

(21) Appl. No.: 15/606,452

(22) Filed: May 26, 2017

(65) Prior Publication Data
US 2017/0345147 A1    Nov. 30, 2017

(30) Foreign Application Priority Data
May 30, 2016    (JP) .................... 2016-107803

(51) Int. Cl.
G06T 7/00       (2017.01)
G06T 7/60       (2017.01)

(52) U.S. Cl.
CPC .............. *G06T 7/0012* (2013.01); *G06T 7/60* (2013.01); *G06T 2207/30036* (2013.01)

(58) Field of Classification Search
CPC combination set(s) only.
See application file for complete search history.

(56) References Cited

U.S. PATENT DOCUMENTS

| 6,250,918 B1 * | 6/2001 | Sachdeva ................. A61C 7/00 433/24 |
| 8,401,826 B2 * | 3/2013 | Cheng ...................... A61C 7/00 703/1 |
| 10,032,271 B2 * | 7/2018 | Somasundaram ... A61B 5/0088 |

(Continued)

FOREIGN PATENT DOCUMENTS

| JP | 9-010231 | 1/1997 |
| JP | 2009-050632 | 3/2009 |

(Continued)

OTHER PUBLICATIONS

Korean Office Action dated Mar. 29, 2018 for corresponding Korean Patent Application No. 10-2017-0066367, with English Translation, 22 pages.

*Primary Examiner* — Anand P Bhatnagar
(74) *Attorney, Agent, or Firm* — Fujitsu Patent Center

(57) ABSTRACT

The tooth axis estimation program includes, extracting a plurality of points from inputted three-dimensional profile data, the plurality of points indicating a surface of three-dimensional profile data; calculating an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of points; and specifying a direction of a tooth included in the region in accordance with the calculated arrangement relationship.

15 Claims, 20 Drawing Sheets

(56) References Cited

U.S. PATENT DOCUMENTS

| | | | |
|---|---|---|---|
| 2005/0019732 A1* | 1/2005 | Kaufmann | A61C 7/00 433/213 |
| 2008/0154419 A1* | 6/2008 | Cheng | A61C 7/00 700/118 |
| 2010/0151404 A1* | 6/2010 | Wu | A61C 7/00 433/24 |
| 2015/0022639 A1* | 1/2015 | Blassnig | G06T 15/06 348/46 |
| 2016/0151026 A1* | 6/2016 | Shibasaki | A61B 6/032 378/10 |
| 2017/0169562 A1* | 6/2017 | Somasundaram | A61B 5/0088 |
| 2017/0325689 A1* | 11/2017 | Salah | G06T 7/251 |

FOREIGN PATENT DOCUMENTS

| | | |
|---|---|---|
| JP | 2010-502246 A | 1/2010 |
| JP | 2010-504169 A | 2/2010 |
| JP | 2014-512891 | 5/2014 |
| WO | 2008/026064 A3 | 3/2008 |
| WO | 2008/036766 A1 | 3/2008 |
| WO | 2012/112867 | 8/2012 |

* cited by examiner

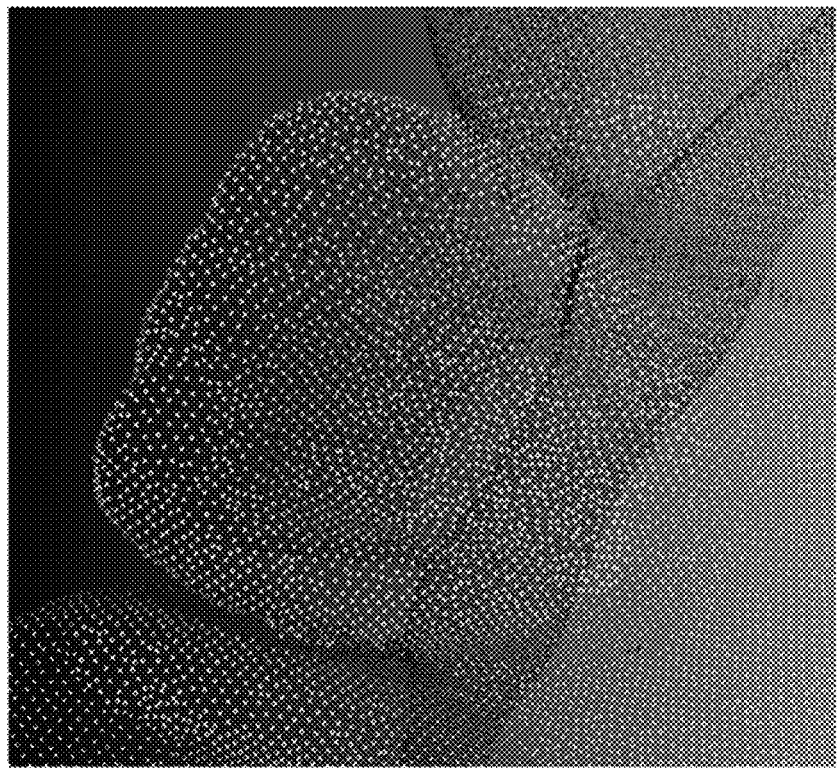
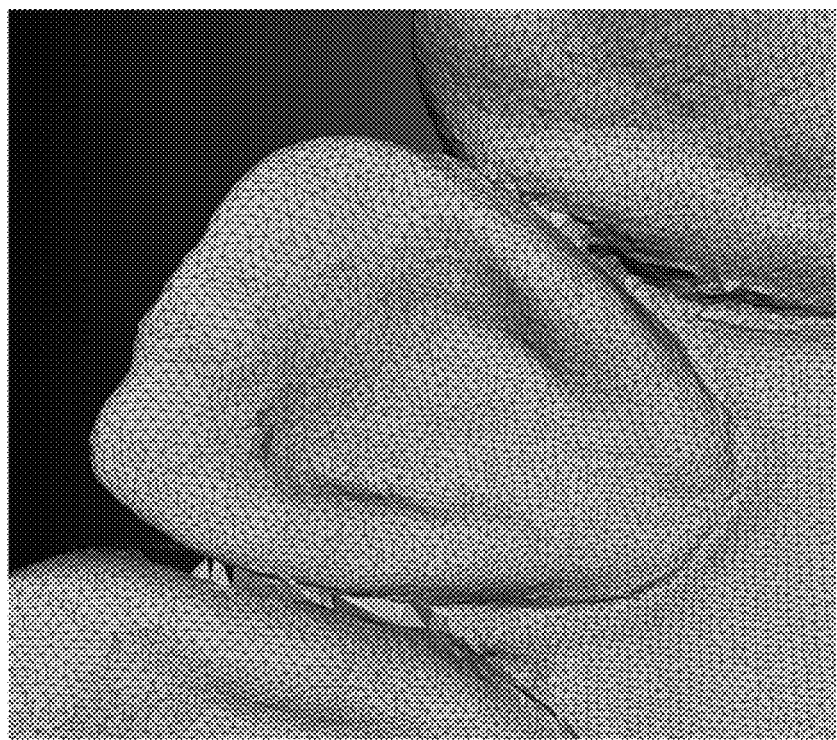

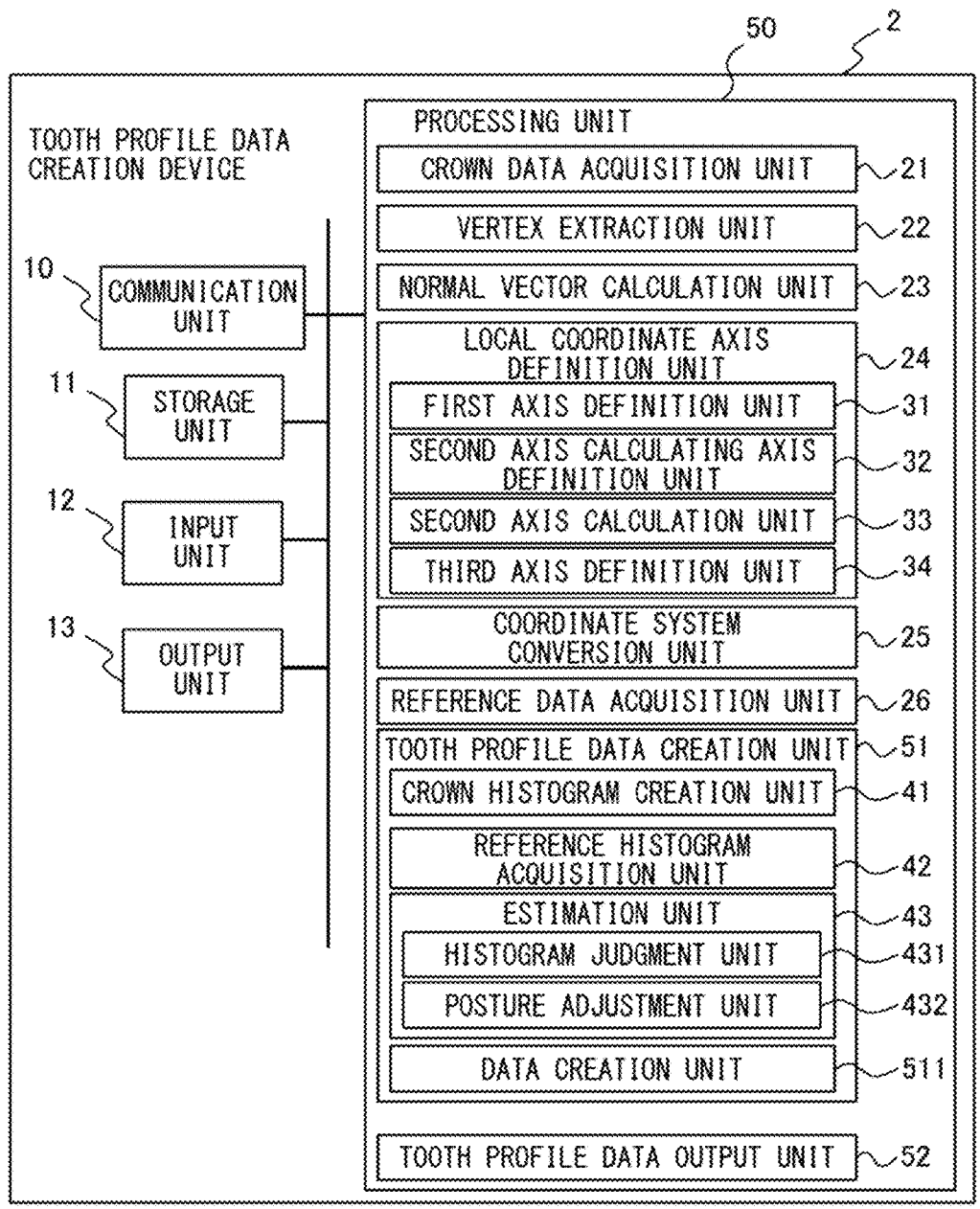

TOOTH AXIS ESTIMATION PROGRAM, TOOTH AXIS ESTIMATION DEVICE AND METHOD OF THE SAME, TOOTH PROFILE DATA CREATION PROGRAM, TOOTH PROFILE DATA CREATION DEVICE AND METHOD OF THE SAME

CROSS-REFERENCE TO RELATED APPLICATION

This application is based upon and claims the benefit of priority of the prior Japanese Patent Application No. 2016-107803, filed on May 30, 2016, the entire contents of which are incorporated herein by reference.

FIELD

The present invention relates to a tooth axis estimation program, a tooth axis estimation device and a method of the same, as well as a tooth profile data creation program, a tooth profile data creation device and a method of the same.

BACKGROUND

It is known to use tooth type data indicating a tooth profile including the crown shape of teeth. For example, it is known to fabricate dental crown prostheses such as crowns and bridges by NC processing from processing data created based on crown profile data selected from a database (see, for example, Patent Literature 1). It is also known to obtain tooth contour information from an unspecified number of survivors in order to identify the identity of unidentified persons caused by disasters, unexpected accidents, etc., and store the tooth contour information in a pre-living database (See, for example, Patent Literature 2).

Further, various techniques of creating oral cavity profile data including crown profile data are known. For example, it is known that by a user assisting a computer to recognize individual teeth by providing input data specifying one or more points on a tooth raw surface, gingival margin data is easily created by the computer (see, for example, Patent Literature 3).

RELATED DOCUMENTS

[Patent Document 1] Japanese Laid Open Patent Document No. H9-10231
[Patent Document 2] Japanese Laid Open Patent Document No. 2009-50632
[Patent Document 3] Japanese Laid Open Patent Document No. 2014-512891

SUMMARY

According to an aspect, the tooth axis estimation program includes, extracting a plurality of points from inputted three-dimensional profile data, the plurality of points indicating a surface of three-dimensional profile data; calculating an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of points; and specifying a direction of a tooth included in the region in accordance with the calculated arrangement relationship.

The object and advantages of the embodiments will be realized and attained by means of the elements and combination particularly pointed out in the claims.

It is to be understood that both the foregoing general description and the following detailed description are exemplary and explanatory and are not restrictive of the invention.

BRIEF DESCRIPTION OF THE DRAWINGS

FIG. 5A is a view illustrating an example of a 3D surface mesh included in crown data;

FIG. 5B is a view illustrating 3D point groups corresponding to the 3D surface mesh illustrated in FIG. 5A;

FIG. 20 is a block diagram of the tooth profile data creation device according to the embodiment;

DESCRIPTION OF EMBODIMENTS

A tooth axis estimation program, a tooth axis estimation device and a method of the same, as well as a tooth profile data creation program, a tooth profile data creation device and a method of the same, will be described hereafter, with reference to the drawings. However, it should be noted that the technical scope of the present invention is not limited to these embodiments, but extends to equivalents with the invention described in the claims.

Outline of the Tooth Axis Estimation Device According to an Embodiment

Figure 1A:
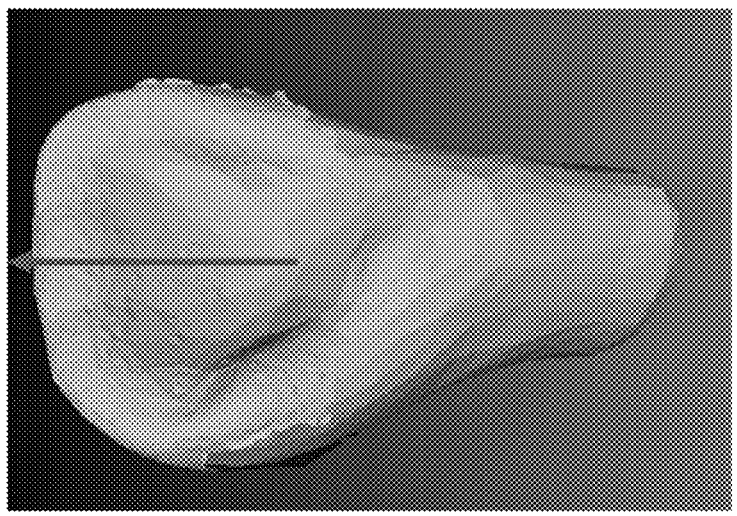
FIG. 1A is a view illustrating an example of a crown shape corresponding to crown data acquired by the tooth axis estimation device according to an embodiment.
Figure 1B:
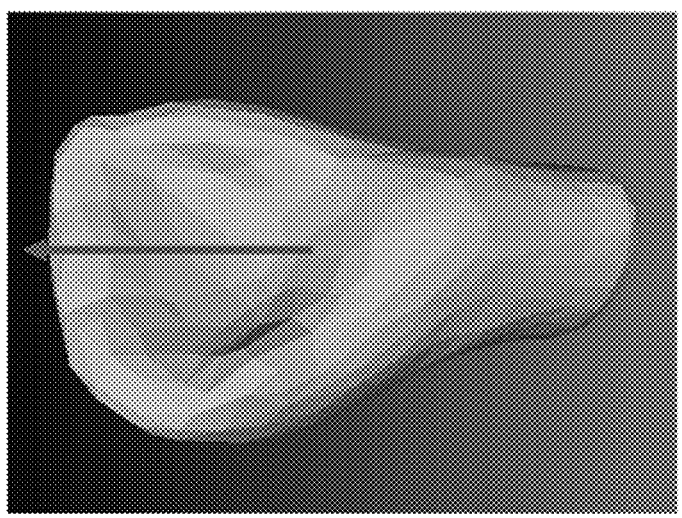
FIG. 1B is a view illustrating an example of a reference shape corresponding to reference data acquired by the tooth axis estimation device according to an embodiment.
Figure 1C:
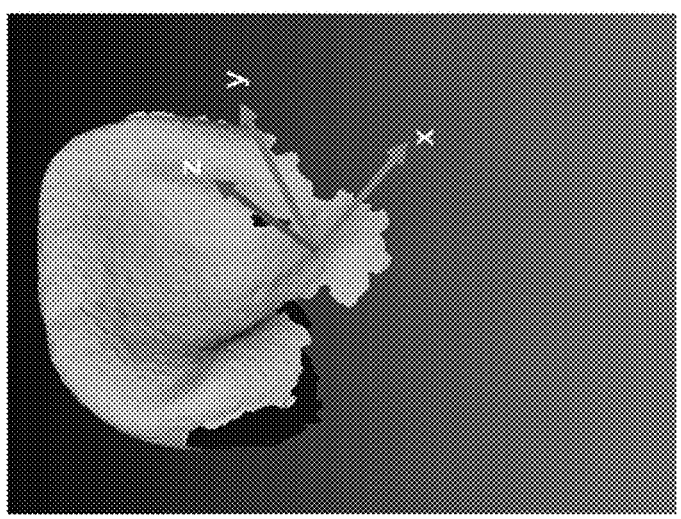
FIG. 1C is a view illustrating a state in which the crown illustrated in FIG. 1A is moved or rotated to coincide with the reference shape illustrated in FIG. 1B.

FIG. 1A is a view illustrating an example of a crown shape corresponding to crown data acquired by the tooth axis estimation device according to an embodiment, and FIG. 1B is a view illustrating an example of a reference shape corresponding to reference data acquired by the tooth axis estimation device according to an embodiment. FIG. 1C is a view illustrating a state in which the crown illustrated in FIG. 1A is moved or rotated to coincide with the reference shape illustrated in FIG. 1B.

The shape of the crown corresponding to the crown data is acquired by a dental 3D scanner (not illustrated). However, as illustrated in FIG. 1A, in the shape of the crown corresponding to the crown data, there is a possibility that a part of the shape is missing. Further, the crown data does not include information regarding a tooth axis indicating an axes along a head and a root of the tooth. On the other hand, the reference data includes data indicating an overall crown shape and also information regarding the tooth axis indicated by an arrow in FIG. 1B.

In the tooth axis estimation device according to the embodiment, a local coordinate indicated by arrows in FIG. 1A are defined on a crown corresponding to crown data, and a crown corresponding to the crown data is moved, rotated, or moved and rotated to coincide with a reference shape corresponding to the reference data. The tooth axis estimation device according to the embodiment is configured to estimate the tooth axis of the crown corresponding to the crown data from a posture of the crown corresponding to the crown data, when the crown corresponding to the crown data is moved, rotated, or moved and rotated to coincide with the reference shape corresponding to the reference data.

The tooth axis estimation device according to the embodiment estimates the tooth axis of the crown from the posture of the crown when the distribution in the normal direction of vertices extracted from the crown data indicating the shape of the crown and the distribution in the normal direction of vertices forming a basic shape corresponding to the reference data, are determined to coincide. The tooth axis estimation device according to the embodiment can estimate the tooth axis of the crown without manual input by a user, by using the crown corresponding to the crown data and distribution in the normal direction of the distribution in the normal direction of vertices forming the basic shape corresponding to the reference data.

Figure 2:
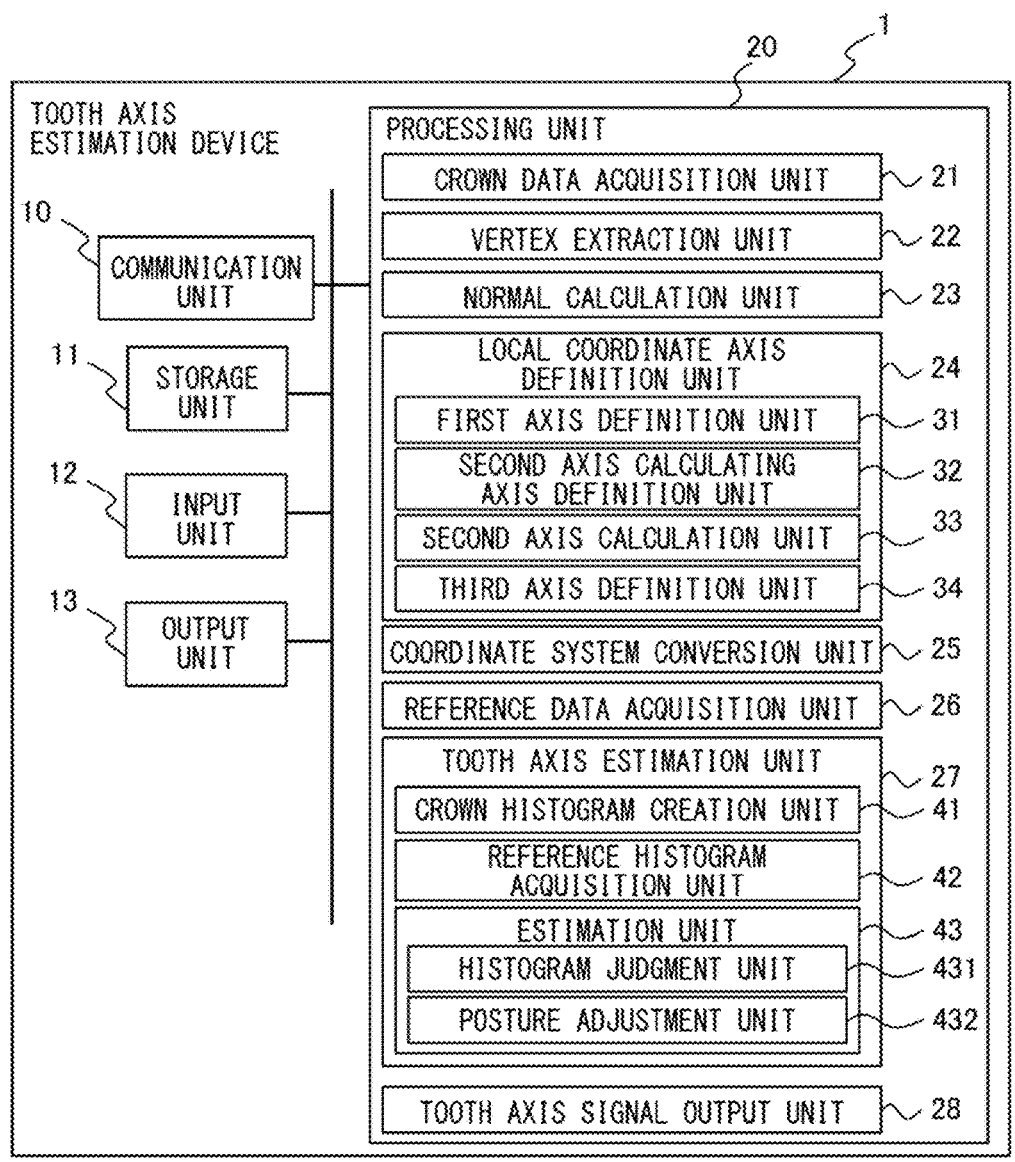
FIG. 2 is a block diagram of a tooth axis estimation device according to an embodiment.

A Configuration and a Function of the Tooth Axis Estimation Device According to an Embodiment FIG. 2 is a block diagram of a tooth axis estimation device according to an embodiment.

A tooth axis estimation device 1 includes a communication unit 10, a storage unit 11, an input unit 12, an output unit 13, and a processing unit 20.

The communication unit 10 communicates with a server (not illustrated) and the like via the Internet according to a protocol of HTTP (Hypertext Transfer Protocol). Then, the communication unit 10 supplies data received from the server or the like to the processing unit 20. Further, the communication unit 10 transmits the data supplied from the processing unit 20 to the server or the like.

The storage unit 11 includes, for example, at least one of a semiconductor device, a magnetic tape device, a magnetic disk device, or an optical disk device. The storage unit 11 stores an operating system program, a driver program, an application program, data, and the like used for processing in the processing unit 20. For example, the storage unit 11 stores a tooth axis estimation program as an application program for causing the processing unit 20 to execute tooth axis estimation processing for estimating the tooth axis. In addition, the storage unit 11 stores a tooth profile data creation program for causing the processing unit 20 to execute tooth profile data creation processing for creating tooth profile data indicating a tooth profile, as an application program. The tooth axis estimation program and the tooth profile data creation program may be installed in the storage unit 11 from a computer-readable portable recording medium such as a CD-ROM, a DVD-ROM or the like using a known setup program or the like.

In addition, the storage unit 11 stores, as data, data or the like to be used in input processing and the like. Further, the storage unit 11 may temporarily store data temporarily used in processing such as input processing.

The input unit 12 may be any device as long as data can be inputted, and may be a touch panel, a key button, or the like for example. An operator can input letters, numbers, symbols, and the like using the input unit 12. When operated by an operator, the input unit 12 generates a signal corresponding to the operation. Then, the generated signal is supplied to the processing unit 20 as an instruction of the operator.

The output unit 13 may be any device as long as it can display images, frames, and the like, for example, and is a liquid crystal display or an organic EL (Electro-Luminescence) display or the like. The output unit 13 displays images corresponding to image data supplied from the processing unit 20, and frames or the like corresponding to moving image data. Further, the output unit 13 may be an output device for allowing images, frames, letters or the like to be printed on the display media such as papers.

The processing unit 20 has one or more processors and peripheral circuits thereof. The processing unit 20 comprehensively controls an overall operation of the tooth axis estimation device 1 and may be, for example, the CPU. The processing unit 20 executes processing based on a program (driver program, operating system program, application program, etc.) stored in the storage unit 11. Further, the processing unit 20 can execute programs (application programs, etc.) in parallel.

The processing unit 20 includes a crown data acquisition unit 21, a vertex extraction unit 22, a normal vector calculation unit 23, a local coordinate axis definition unit 24, a coordinate system conversion unit 25, a reference data acquisition unit 26, a tooth axis estimation unit 27 and a tooth axis signal output unit 28. The local coordinate axis definition unit 24 has a first axis definition unit 31, a second axis calculating axis definition unit 32, a second axis calculation unit 33, and a third axis definition unit 34. The tooth axis estimation unit 27 includes a crown histogram creation unit 41, a reference histogram acquisition unit 42, and an estimation unit 43. The estimation unit 43 includes a histogram judgment unit 431 and a posture adjustment unit 432. Each of these units is a functional module realized by a program executed by a processor included in the processing unit 20. Alternatively, each of these units may be mounted on the tooth axis estimation device 1 as firmware.

Operation of the Tooth Axis Estimation Device According to an Embodiment

Figure 3:
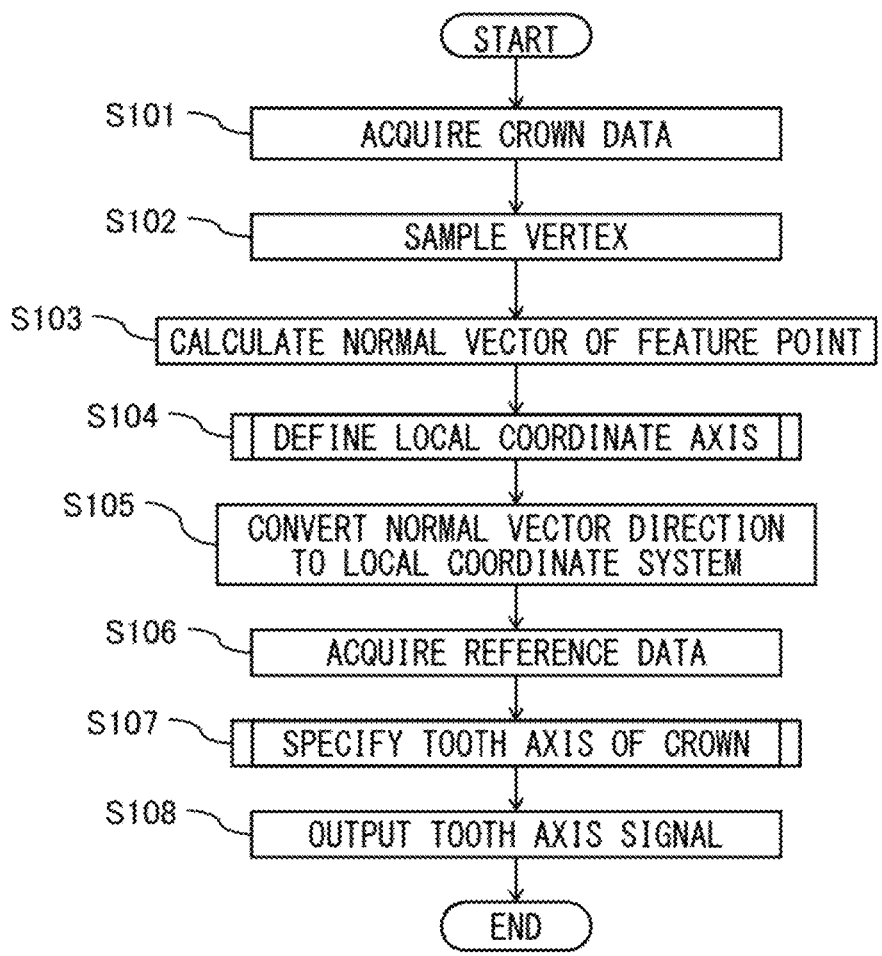
FIG. 3 is a flowchart of the tooth axis estimation processing performed by the tooth axis estimation device illustrated in FIG. 2.

FIG. 3 is a flowchart of the tooth axis estimation processing performed by the tooth axis estimation device 1. The tooth axis estimation processing illustrated in FIG. 3 is executed mainly by the processing unit 20 in cooperation with each element of the tooth axis estimation device 1, based on a program stored in the storage unit 11 in advance.

The process of S101 includes a process of extracting point groups indicating the surface of the three-dimensional profile data, from the inputted three-dimensional profile data. The processes of S102 to S107 includes processes of moving and/or rotating the three-dimensional profile data of a tooth corresponding to a specific type of tooth, calculating an arrangement relationship in which an error between a point group included in any of a region of the extracted point groups and three-dimensional profile data of a tooth becomes minimum, and estimating a direction of the tooth included in this region based on the calculated arrangement relationship.

First, the crown data acquisition unit 21 acquires crown data indicating the shape of the crown including vertices (S101).

Figure 4:
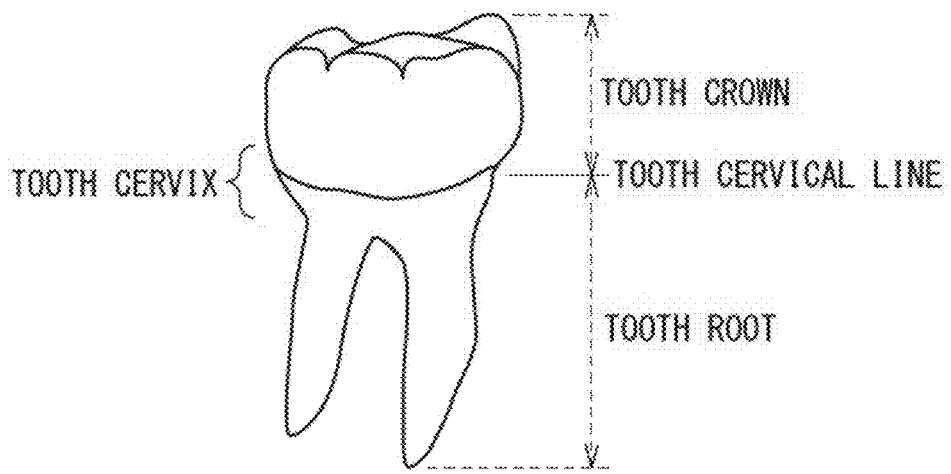
FIG. 4 is a perspective view of a tooth.

FIG. 4 is a perspective view of a tooth, FIG. 5A is a view illustrating an example of a 3D surface mesh included in crown data, and FIG. 5B is a view illustrating 3D point groups corresponding to the 3D surface mesh illustrated in FIG. 5A.

The crown is a portion of the entire teeth, appears to the outside from a gingiva, is exposed (erupted) into an oral cavity, and is covered with enamel. A part below the crown is called a "tooth root" and a boundary line between the crown and tooth root is called a "tooth cervical line".

Tooth type scan data 501 is acquired by use of a dental 3D scanner (not illustrated), as tooth type information of each of an unspecified majority. As an example, the tooth type scan data 501 is acquired as dental CAD (Computer Aided Design)/CAM (Computer Aided Manufacturing) data at dental laboratories, dental clinics and the like. The tooth type scan data 501 is stored in the storage unit 11 in a file format such as stl, ply, off, and 3 ds, etc. The tooth type scan data 501 is an aggregate of triangular polygons. The 3D point group data 502 includes vertices corresponding to the vertices of the triangular polygon included in the tooth type scan data 501.

Next, the vertex extraction unit 22 uniformly, i.e., evenly samples the vertices included in an analysis target region of the tooth type scan data from an entire region of the aggregate (S102). As an example, the vertex extraction unit 22 samples about 200 thousand to 600 thousand vertices included in the analysis target region of the tooth type scan data and extracts about 10 thousand feature points. The vertex extraction unit 22 extracts the point groups indicating the surface of the three-dimensional profile data, from the inputted three-dimensional profile data, by the process of S102.

Figure 6:
FIG. 6 is a view illustrating an example of the feature points extracted by the vertex extraction unit illustrated in FIG. 2.

FIG. 6 is a view illustrating an example of the feature points extracted by the vertex extraction unit 22. In FIG. 6, the feature points are indicated by black spots.

Next, the normal vector calculation unit 23 calculates a normal vector of the feature points extracted by the process of S102 (S103). The normal vector calculation unit 23 calculates the normal vector of the feature points, by weighting the each directions of the normal vector of triangular polygons including a feature point, according to areas of the polygons.

Figure 7:
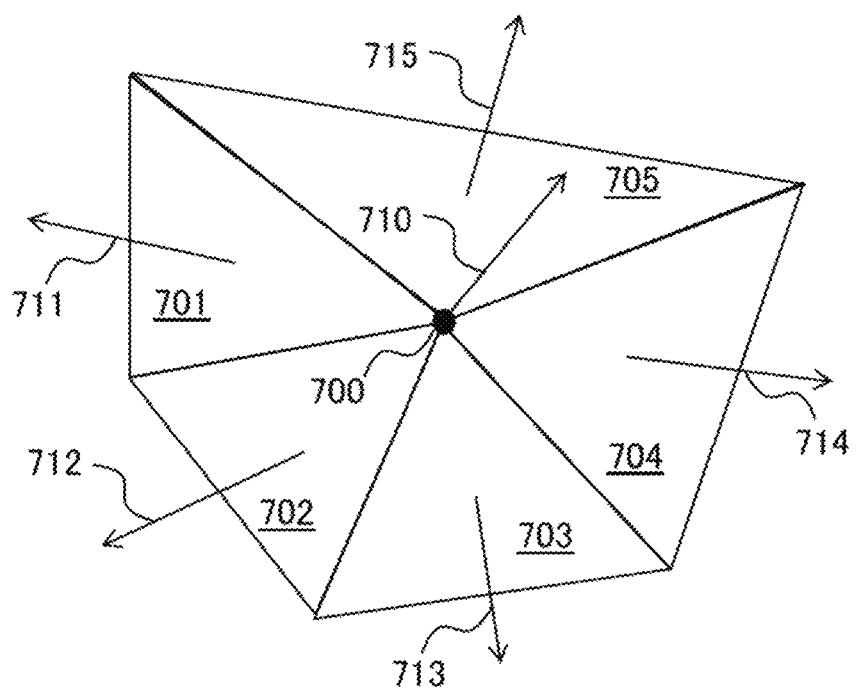
FIG. 7 is a view illustrating an example of processing of calculating the normal vector of the feature points.

FIG. 7 is a view illustrating an example of processing of calculating the normal vector of the feature points.

Feature points 700 are vertices of five polygons, i.e., a first polygon 701, a second polygon 702, a third polygon 703, a fourth polygon 704, and a fifth polygon 705. A first normal vector 711 is the normal vector of a first polygon 701, a second normal vector 712 is the normal vector of a second polygon 702, and a third normal vector 713 is the normal vector of a third polygon 703. Further, a fourth normal vector 714 is the normal vector of a fourth polygon 704, and a fifth normal vector 715 is the normal vector of a fifth polygon 705. The first normal vector 711, the second normal vector 712, the third normal vector 713, the fourth normal vector 714, and the fifth normal vector 715 have the same unit lengths.

The normal vector calculation unit 23 calculates the direction of the normal vector 710 of the feature point 700 by weighting each of the first normal vector 711 to the fifth normal vector 715 with each of the areas of the first polygon 701 to the fifth polygon 705. The normal vector 710 of the feature point 700 has the unit length as with the first normal vector 711 to the fifth normal vector 715.

Figure 8:
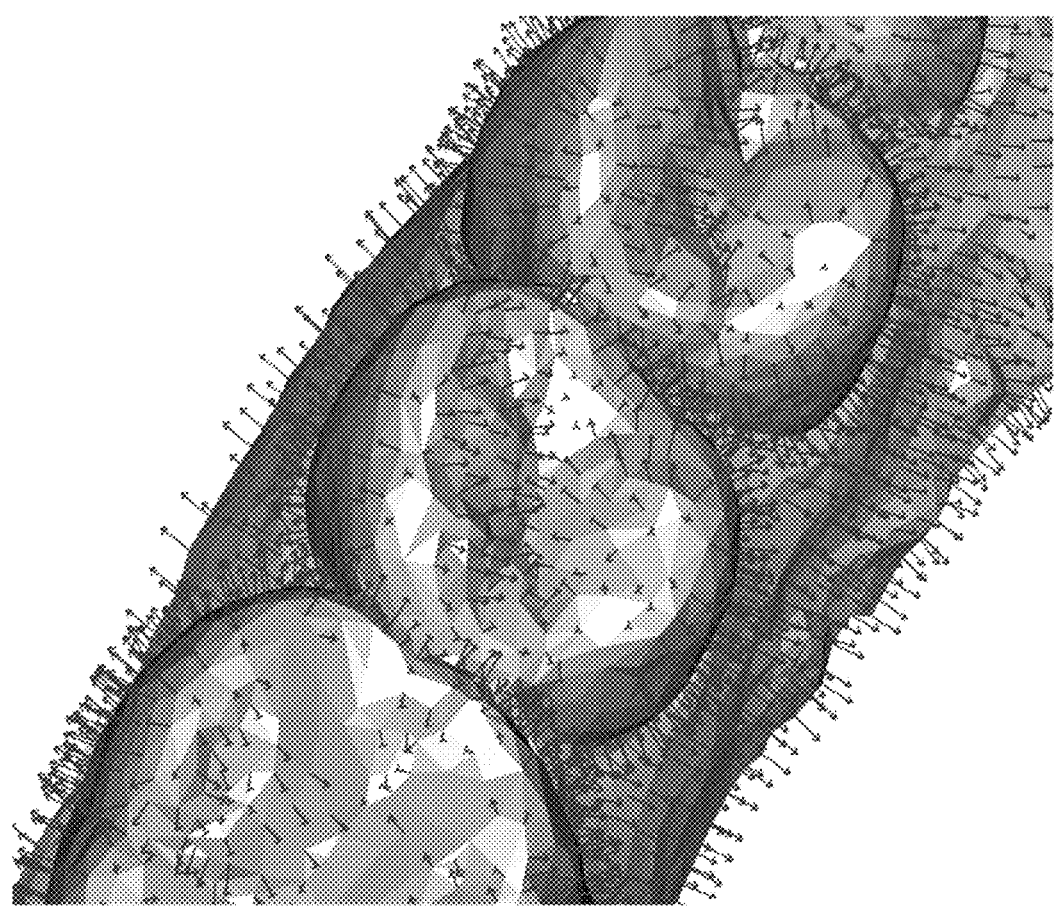
FIG. 8 is a view illustrating an example of the normal vectors of the feature points calculated in the process of S103 illustrated in FIG. 3.

FIG. 8 is a view illustrating an example of the normal vectors of the feature points calculated in the process of S103. The normal vectors of the feature points are calculated in the process of S103, i.e., the directions of the normal vectors of the triangular polygons including a feature point are weighted according to the areas of the polygons for calculation, and all of the normal vectors have the same unit lengths.

Next, for each of the feature points, the local coordinate axis definition unit 24 defines a local coordinate axis based on the distribution in the direction of the normal vector calculated in the process of S103 (S104).

Figure 9:
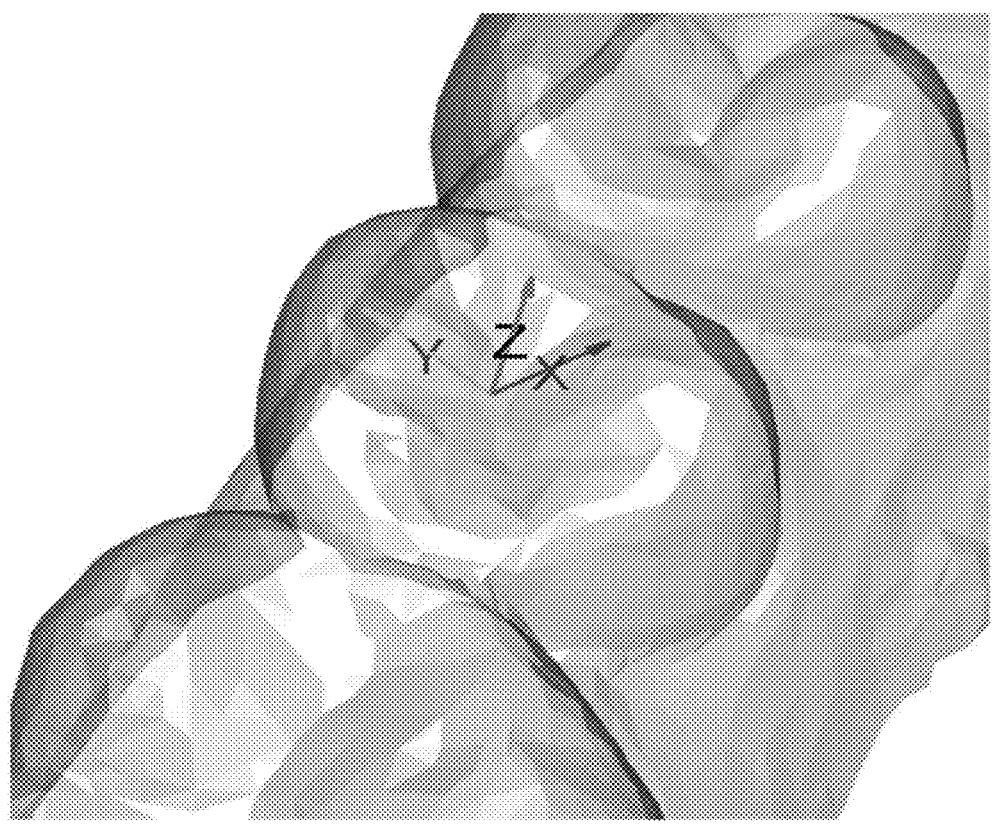
FIG. 9 is a view illustrating an example of the local coordinate system calculated in the process of S104 illustrated in FIG. 3.

FIG. 9 is a view illustrating an example of the local coordinate system (Local Reference Frame, LRF) calculated in the process of S104.

In the local coordinate system, X direction is defined as a direction in which the distribution in the direction of the normal vector calculated in the process of S103 is most varied, in other words, the direction in which the variance is the largest. Further, Y direction is a direction orthogonal to the X direction, and Z direction is a direction orthogonal to both the X direction and the Y direction.

Next, the coordinate system conversion unit 25 converts the directions of the normal vectors of the feature points calculated in the process of S103 for each of the feature points, to the local coordinate system calculated in the process of S104 (S105).

Figure 10:
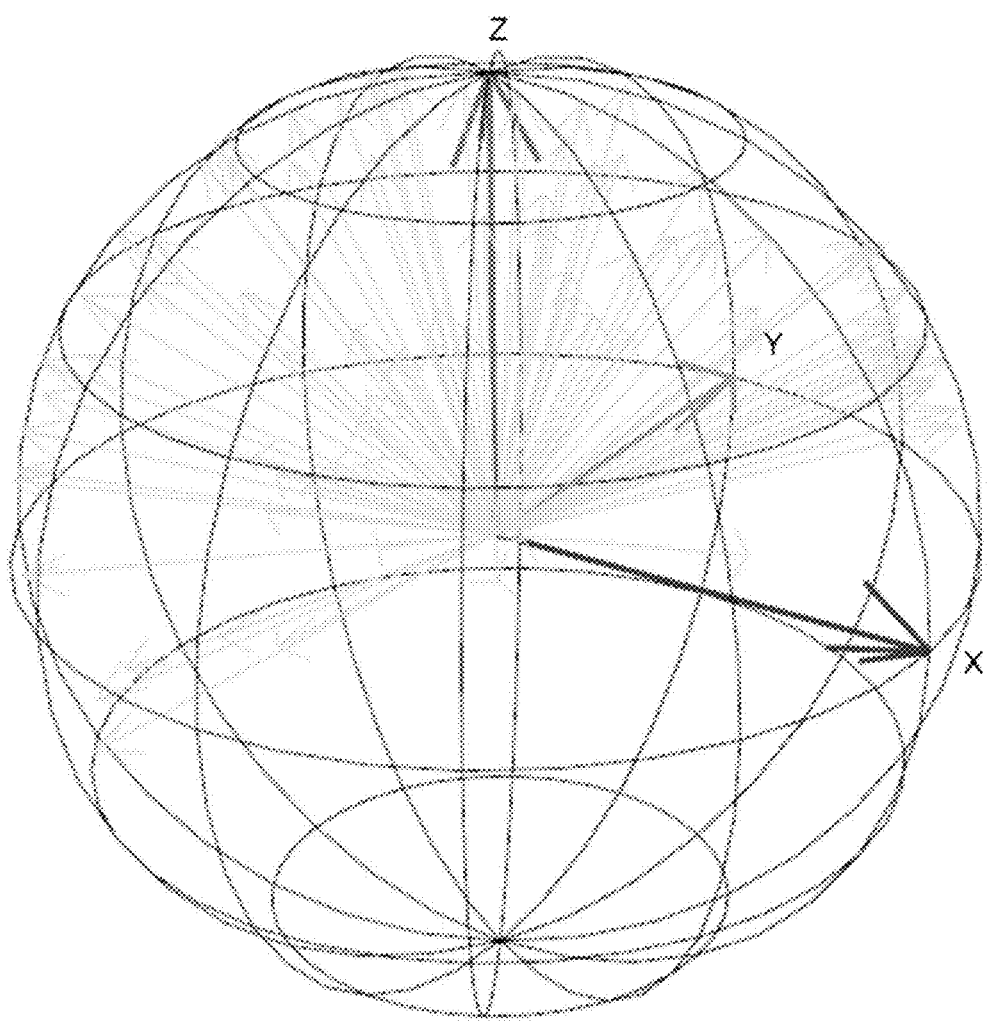
FIG. 10 is a histogram illustrating the directions of the normal vectors of the feature points converted to the polar coordinates system in the process of S105 illustrated in FIG. 3.

FIG. 10 is a histogram illustrating the directions of the normal vectors of the feature points converted to the polar coordinates system in the process of S105. The histogram illustrated in FIG. 10 is also referred to as a SHOT descriptor.

The coordinate system conversion unit 25 can indicate a shape around the feature points, by describing a start point of each of the normal vectors of the feature points calculated in the process of S103 as an origin, and describing an end point of each of the normal vectors of the feature points as a spherically arranged histogram.

The reference data acquisition unit 26 acquires reference data indicating a reference shape including vertices, respective normal vectors of the vertices, and a tooth axis (S106). The reference shape corresponding to the reference data is also referred to as a template model and includes shapes which are the shapes of the same tooth and have different shapes from each other.

Figure 11:
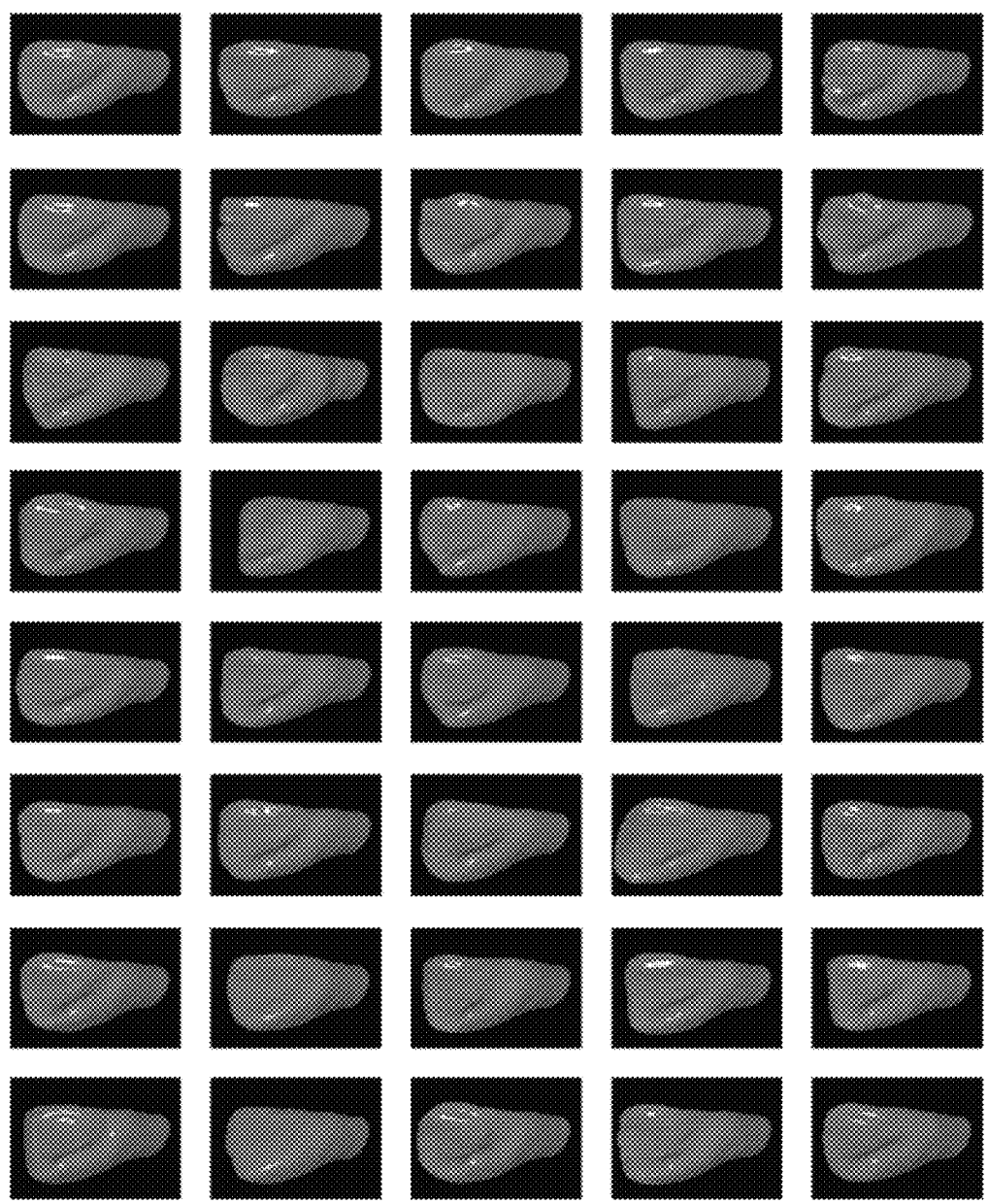
FIG. 11 is a view illustrating an example of template models included in the reference shape.

FIG. 11 is a view illustrating an example of template models included in the reference shape. FIG. 10 illustrates forty template models.

It is preferable that the template models included in the reference data acquired by the reference data acquisition unit 26 have shapes different from each other for the same teeth. An analogy of the shape of the template model included in the reference data, may be judged based on a "voting" explained in Section 3 of "Object Recognition in 3D Scenes with Occlusions and Clutter by Hough Voting" F. Tombari and L. D. Stefano (2012)".

Next, the tooth axis estimation unit 27 specifies the tooth axis of the crown from the posture of the crown when the distribution in the direction of the normal vector calculated in the process of S103, and the distribution in the direction of the normal vector of vertices forming the basic shape corresponding to the reference data, are judged to coincide (S107).

Then, the tooth axis signal output unit 28 outputs a tooth axis signal indicating the tooth axis specified in the process of S107 (S108).

Figure 12:
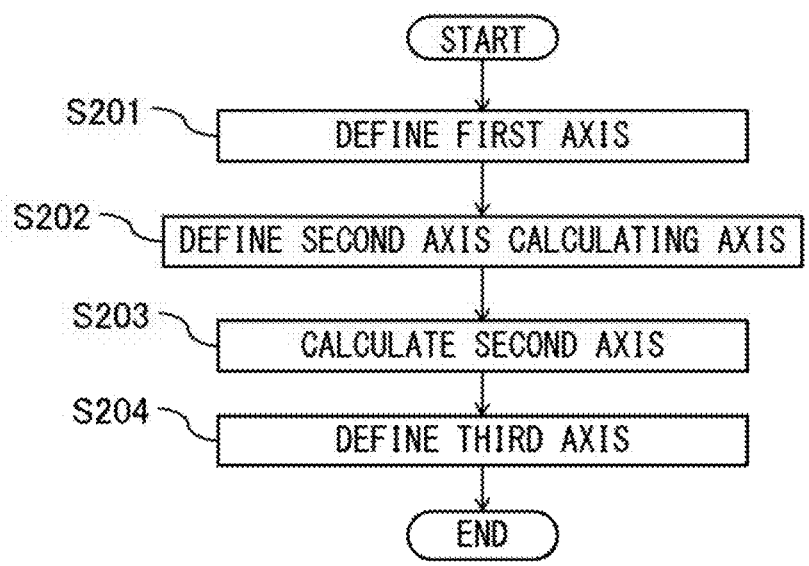
FIG. 12 is a flowchart illustrating more detailed processing than the process of S104 illustrated in FIG. 3.

FIG. 12 is a flowchart illustrating more detailed processing than the process of S104.

First, the first axis definition unit 31 defines the X axis which is a first axis in a direction in which the calculated variance in the direction of the normal vector becomes maximum (S201).

Figure 13B:
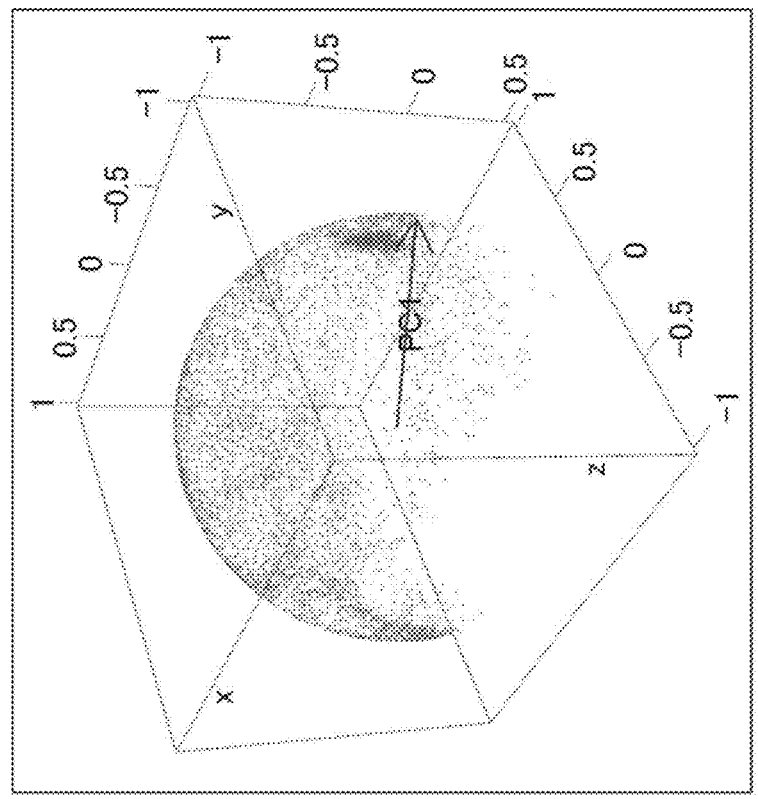
FIG. 13B is a view illustrating an example of the X axis defined for the crown.
Figure 13A:
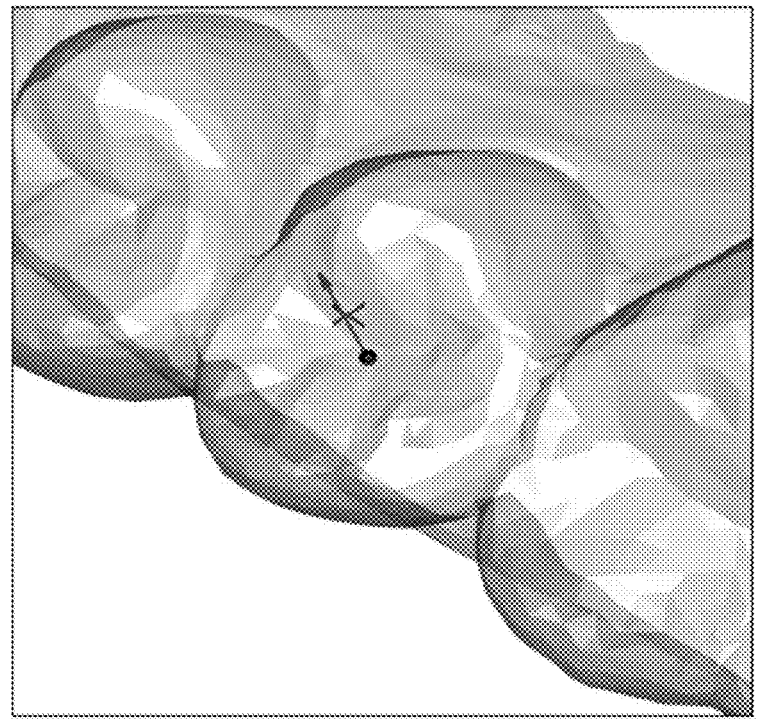
FIG. 13A is a view illustrating an example of the X axis defined in the SHOT descriptor.

FIG. 13A is a view illustrating an example of the X axis defined in the SHOT descriptor, and FIG. 13B is a view illustrating an example of the X axis defined for the crown.

In the example illustrated in FIG. 13(*a*), there are many normal vectors in both the extending direction of the X-axis PC1 and the direction opposite to the extending direction of the X-axis PC1, and therefore the extending direction of the X-axis PC1 is the direction in which the variance in the direction of the normal vector becomes maximum.

Next, the second axis calculating axis definition unit 32 defines a second axis calculating axis N used for calculating the second axis in a direction in which the calculated variance in the direction of the normal vectors becomes minimum (S202). The second axis calculating axis definition unit 32 defines the second axis calculating axis N in the direction in which the calculated variance in the direction of the normal vectors becomes minimum, i.e., in a direction in which the directions of the normal vectors are averaged. The second axis calculating axis N is an axis used for determining the direction of the second axis, i.e., the Y axis.

Figure 14:
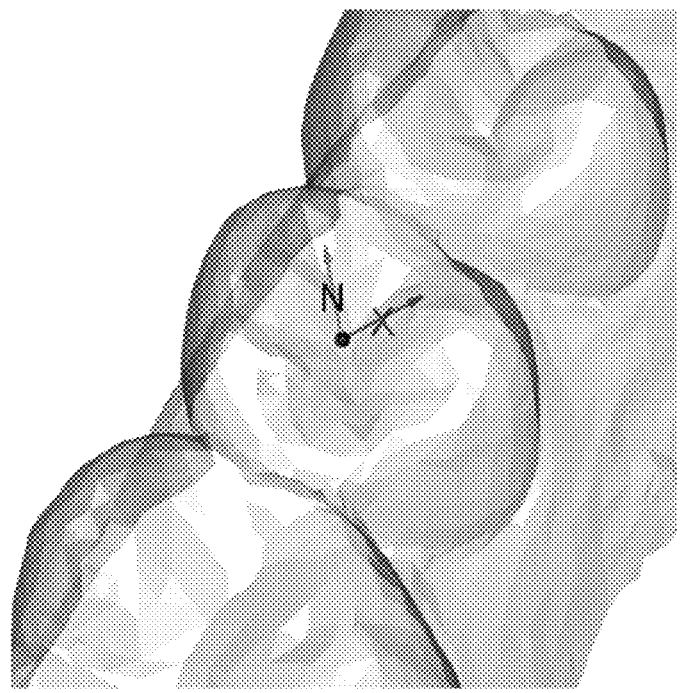
FIG. 14 is a view illustrating an example of the X axis and the second axis calculating axis N defined for the crown.

FIG. 14 is a view illustrating an example of the X axis and the second axis calculating axis N defined for the crown.

Since the second axis calculating axis N extends in a direction in which the calculated variance in the direction of the normal vectors becomes minimum, the extending direction of the X axis and the extending direction of the second axis calculating axis N are not always orthogonal.

Next, the second axis calculation unit 33 calculates the second axis, i.e., the Y axis, from an outer product of the X axis and the second axis calculating axis N (S203). The second axis calculation unit 33 calculates a direction which is orthogonal to the X axis and is also orthogonal to the second axis calculating axis N, as the Y axis direction.

Figure 15:
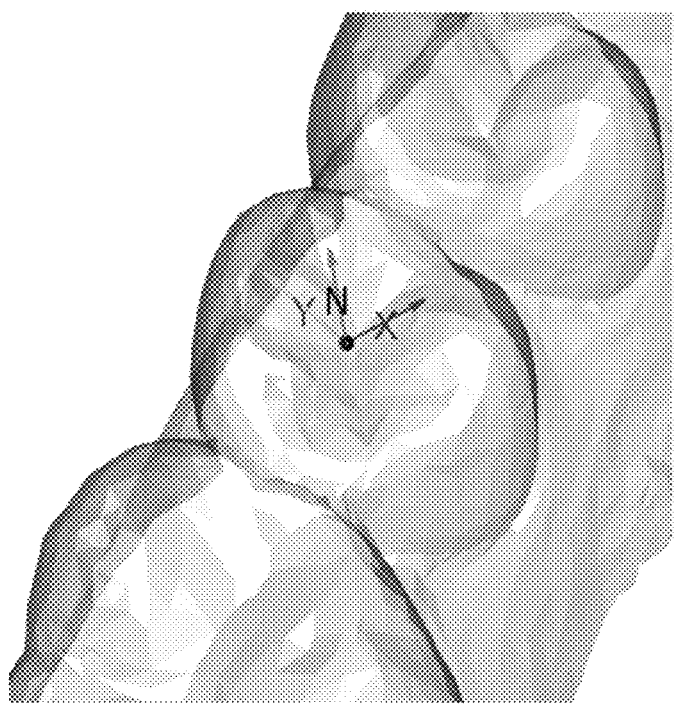
FIG. 15 is a view illustrating an example of the X axis, the second axis calculating axis N and the Y axis defined for the crown.

FIG. 15 is a view illustrating an example of the X axis, the second axis calculating axis N and the Y axis defined for the crown. The Y axis extends in a direction which is orthogonal to the X axis and is also orthogonal to the second axis calculating axis N.

Then, a third axis definition unit 34 defines the Z axis which is a third axis in a direction orthogonal to both the X axis and the Y axis (S204).

Figure 16:
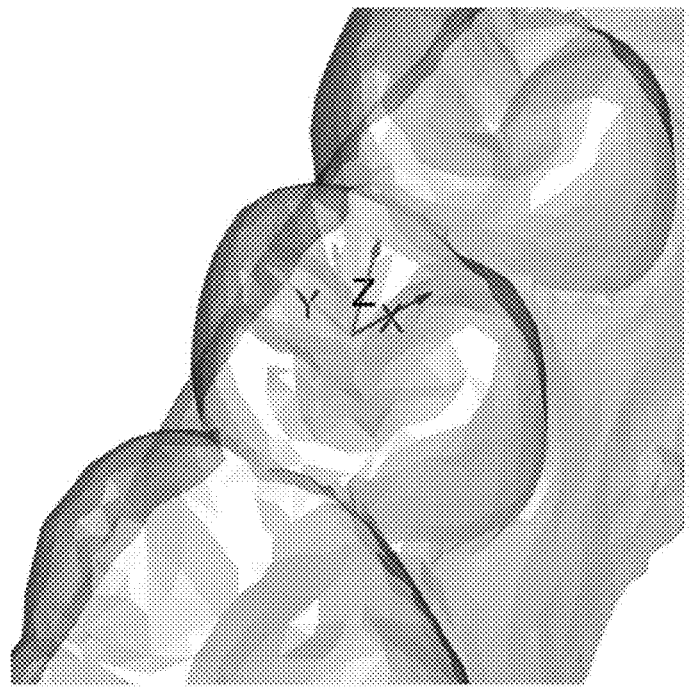
FIG. 16 is a view illustrating an example of the X axis, the second axis calculating axis N, the Y axis and the Z axis defined for the crown.

FIG. 16 is a view illustrating an example of the X axis, the second axis calculating axis N, the Y axis and the Z axis defined for the crown. The Z axis extends in a direction which is orthogonal to the X axis and is also orthogonal to the Y axis.

Figure 17:
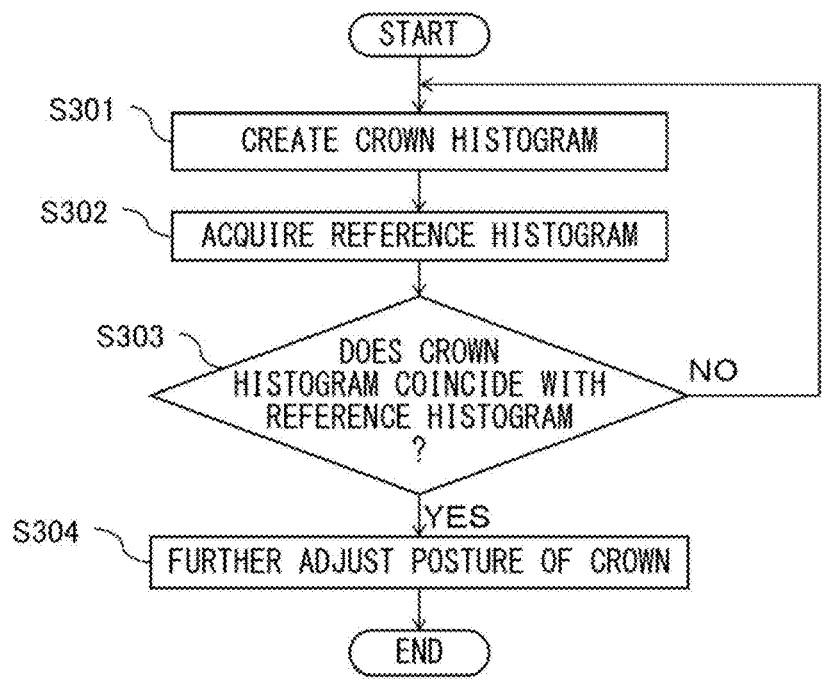
FIG. 17 is a flowchart illustrating more detailed processing than the process in S107 illustrated in FIG. 3.

FIG. 17 is a flowchart illustrating more detailed processing than the process in S107.

First, the crown histogram creation unit 41 creates a crown histogram which is a two-dimensional histogram indicating the distribution in the direction of the normal vector calculated in the process of S103 when the crown is moved or rotated (S301). Next, the reference histogram acquisition unit 42 acquires a reference histogram which is a two-dimensional histogram indicating the normal vector distribution of vertices of a region corresponding to an analysis target region having a reference shape (S302).

Figure 18A:
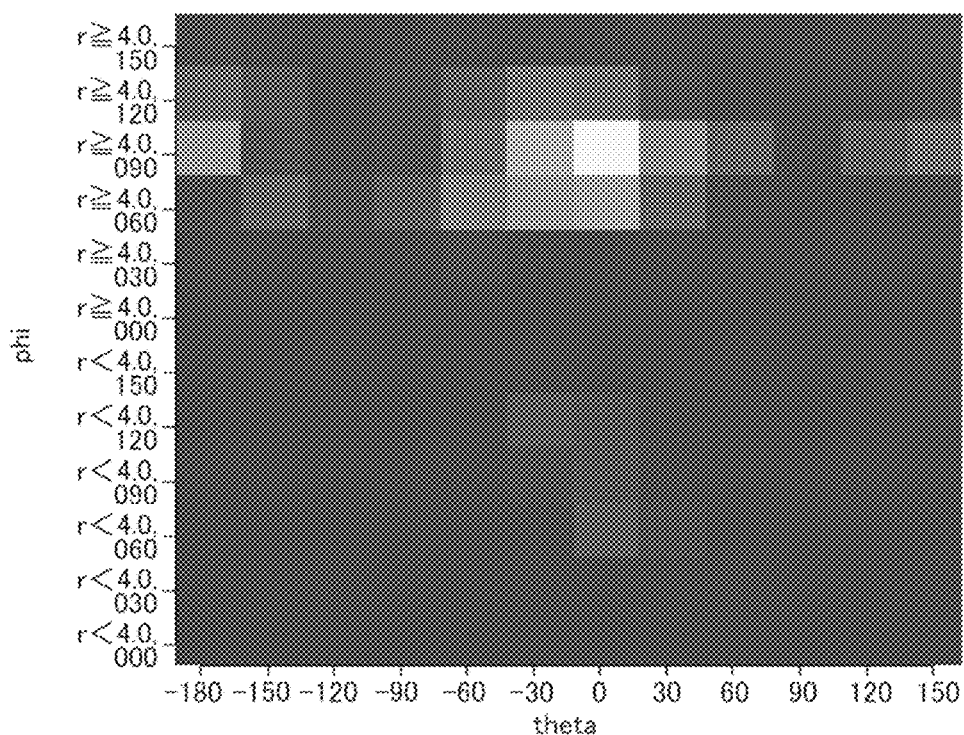
FIG. 18A is a view illustrating an example of the two-dimensional histogram.
Figure 18B:
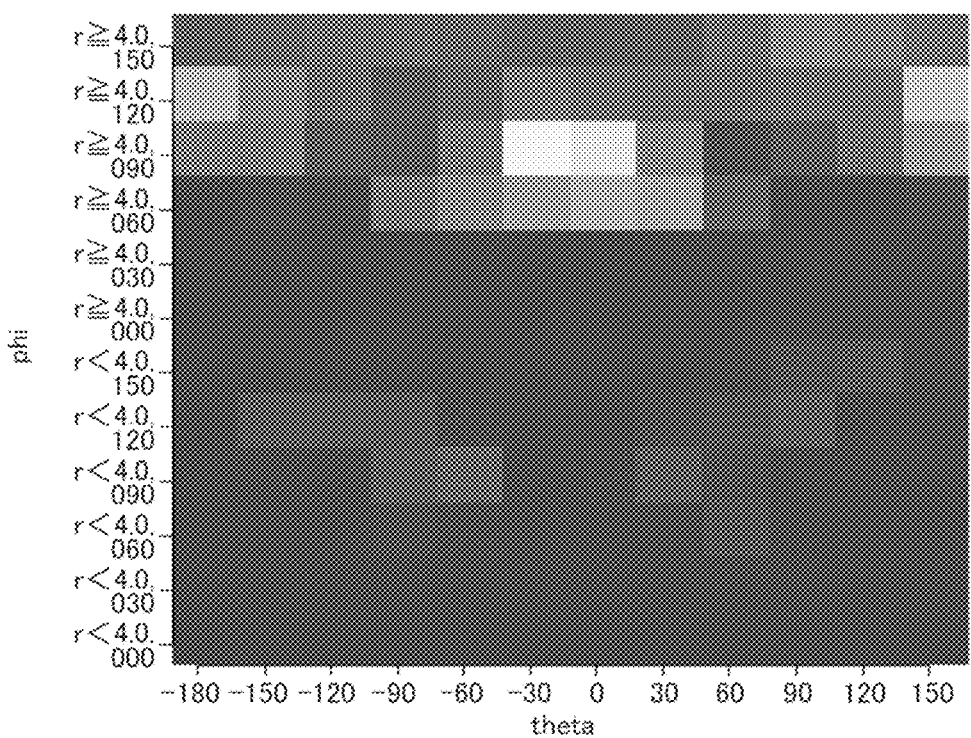
FIG. 18B is a view illustrating another example of the two-dimensional histogram.

FIG. 18A is a view illustrating an example of the two-dimensional histogram, and FIG. 18B is a view illustrating another example of the two-dimensional histogram. In FIGS. 18A and 18B, the horizontal axis and the vertical axis indicate deflection angles $\theta$ and $\phi$ of a polar coordinate system of the feature points converted in the process of S105 respectively.

FIG. 18A illustrates an example of the two-dimensional histogram corresponding to the number 11 indicated by the number defined by the FDI (Federation dentaire internationale) notation. FIG. 18B illustrates an example of the two-dimensional histogram corresponding to the number 14 defined by the FDI notation.

Next, the histogram judgment unit 431 judges whether the crown histogram acquired in the process of S301 coincides with the reference histogram acquired in the process of S301 (S303). When it is judged that the crown histogram and the reference histogram do not coincide with each other (S303—NO), the process returns to S301. Thereafter, the processes of S301 to S303 are repeated until it is judged that the crown histogram and the reference histogram coincide with each other (S303—YES).

Every time the processes are repeated, the crown histogram creation unit 41 changes a position in which the crown is moved or a direction and an angle in which the crown is rotated in the process of S301, thereby changing the posture of the crown to create a crown histogram.

When it is judged that the crown histogram and the reference histogram do not coincide with each other in the process of S303 even if the posture of the crown is changed in the process of S301, the reference histogram acquisition unit 42 acquires the reference histogram when the reference shape is enlarged or shrunk. Further, the reference histogram acquisition unit 42 acquires the reference shape having other shapes included in the reference data when it is judged that the crown histogram and the reference histogram do not coincide with each other even if the reference histogram when the reference shape is enlarged or shrunk is acquired.

When it is judged that the crown histogram and the reference histogram coincide with each other (S303—YES), the posture adjustment unit 432 further adjusts the posture of the crown when the crown histogram and the reference histogram are judged to coincide with each other, so as to coincide with the reference shape (S304). As an example, the posture adjustment unit 432 may further adjust the posture of the crown so as to coincide with the reference shape using an ICP algorithm.

A Function Effect of the Tooth Axis Estimation Device According to the Embodiment The tooth axis estimation device 1 can estimate the position of the crown without manual input by a user, using the distribution in the direction of the normal vector of each of the feature points.

In addition, by acquiring the reference data indicating the reference shapes including shapes that differ in shape from each other, the tooth axis estimation device 1 can use other reference shapes when the shape of the posture of the crown and one reference shape do not coincide with each other even if the posture of the crown is changed.

In addition, the tooth axis estimation device 1 estimates the tooth axis of the crown using the crown histogram indicating the distribution in the direction of the normal vector when the posture of the crown is changed, and therefore the processing of the crown data including many vertices becomes easy.

The tooth axis estimation device 1 further adjusts the posture of the crown when the crown histogram and the reference histogram are judged to coincide with each other, in order for the posture of the crown to coincide with the reference shape. Therefore, estimation accuracy of the tooth axis can be improved.

Further, according to the tooth axis estimation device 1, the direction of the normal vector of the vertex is calculated by weighting the each directions of the normal vectors of the polygons including the vertex according to the areas of the polygons, and therefore the direction of the normal vector is calculated in consideration of the areas of the polygons including the vertex.

Further, when the local coordinate system used for creating the SHOT descriptor is defined, the tooth axis estimation device 1 defines the second axis calculating axis used for calculating the second axis in the direction in which the variance in the direction of the normal vectors becomes minimum, and calculates the second axis from the outer product of the first axis and the second axis calculating axis. By using the second axis calculating axis when the second axis is calculated, the SHOT descriptor can be created with high reproducibility.

Outline of the Tooth Profiled Data Creation Device According to an Embodiment

Figure 19A:
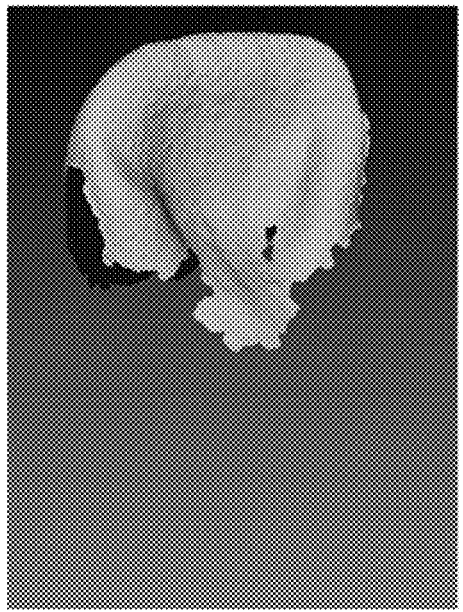
FIG. 19A is a view illustrating an example of the shape of the crown corresponding to the crown data acquired by the tooth profile data creation device according to the embodiment.
Figure 19B:
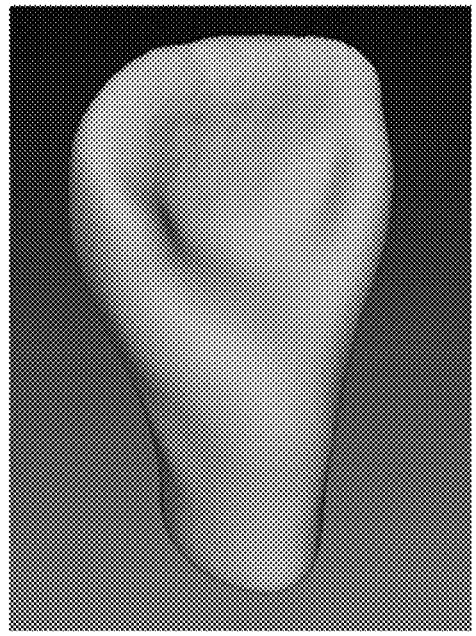
FIG. 19B is a view illustrating an example of the tooth profile corresponding to the tooth profile data created from the crown illustrated in FIG. 19A.

FIG. 19A is a view illustrating an example of the shape of the crown corresponding to the crown data acquired by the tooth profile data creation device according to the embodiment, and FIG. 19B is a view illustrating an example of the tooth profile corresponding to the tooth profile data created from the crown illustrated in FIG. 19A.

The tooth profile data creation device according to the embodiment moves, rotates, or moves and rotates the crown corresponding to the crown data to cause the crown to coincide with the reference shape corresponding to the reference data. The tooth profile data creation device according to the embodiment creates the tooth profile data indicating a tooth profile based on the crown point group including the vertex corresponding to the posture of the crown when the crown coincides with the reference shape corresponding to the reference data, and the reference point group including the vertex corresponding to the reference shape.

The tooth profile data creation device according to the embodiment can create a crown model in which only an occlusal surface is changed by creating the tooth profile data from the crown corresponding to the crown data.

Configuration and Function of the Tooth Profile Data Creation Device According to an Embodiment FIG. 20 is a block diagram of the tooth profile data creation device according to the embodiment.

The tooth profile data creation device 2 is different from the tooth axis estimation device 1 in that the former includes the processing unit 50 in place of the processing unit 20. The processing unit 50 differs from the processing unit 20 in that the former includes the tooth profile data creation unit 51 and the tooth profile data output unit 52 in place of the tooth axis estimation unit 27 and the tooth axis signal output unit 28. The configurations and functions of the components of the tooth profile data creation device 2 other than the tooth profile data creation unit 51 and the tooth profile data output unit 52 are the same as those of the components of the tooth axis estimation device 1 denoted by the same reference numerals, and therefore a detailed explanation will be omitted here. The tooth profile data creation unit 51 is different from the tooth axis estimation unit 27 in that the former includes the data creation unit 511.

Operation of the Tooth Profile Data Creation Device According to an Embodiment

Figure 21:
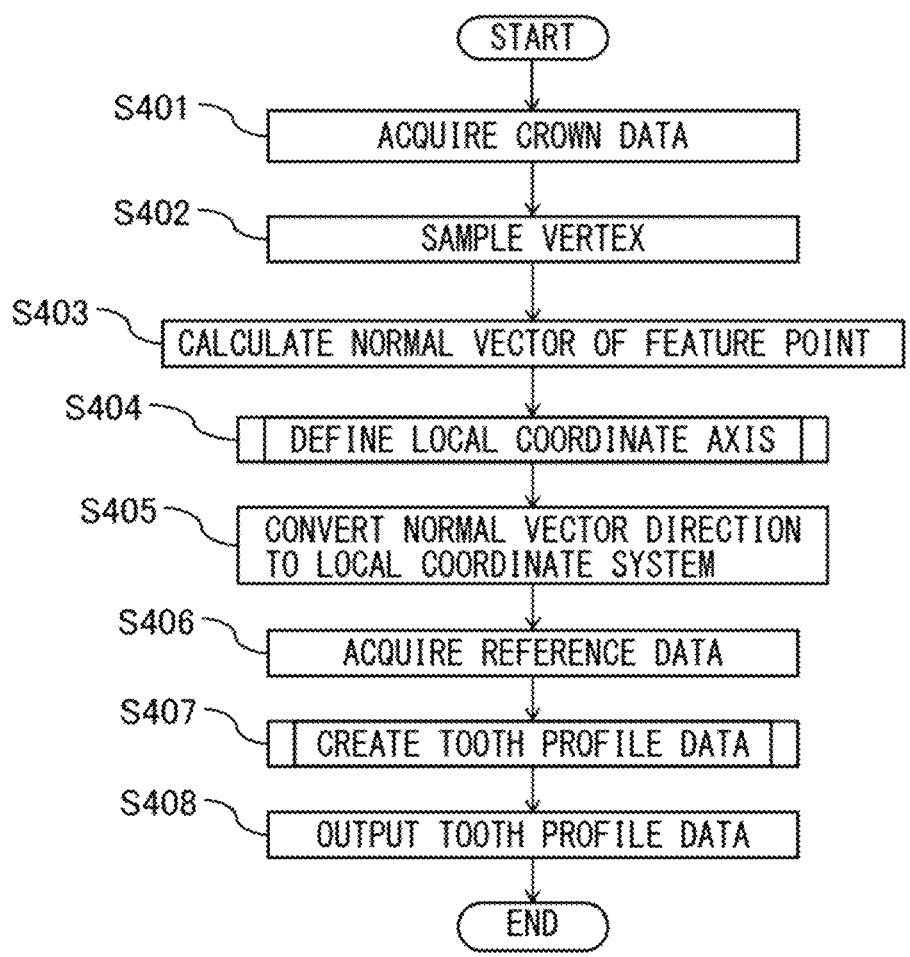
FIG. 21 is a flowchart of the tooth profile data creation processing by the tooth profile data creation device illustrated in FIG. 20.

FIG. 21 is a flowchart of the tooth profile data creation processing by the tooth profile data creation device 2. The tooth profile data creation processing illustrated in FIG. 3 is executed mainly by the processing unit 50 in cooperation with each element of the tooth profile data creation device 2, based on a program stored in advance in the storage unit 11.

The processes of S401 to S406 are the same as the processes of S101 to S106, and therefore a detailed explanation thereof will be omitted here.

In the process of S407, first, the tooth profile data creation unit 51 determines the posture of the crown when distribution in the direction of the normal vector calculated in the process of S403 and the distribution in the direction of the normal vector of vertices forming a basic shape corresponding to the reference data, are judged to coincide with each other. Then, the tooth profile data creation unit 51 creates the tooth profile data indicating the tooth profile, based on the crown point group including the vertex corresponding to the determined posture of the crown, and the reference point group including the vertex corresponding to the reference shape (S407). Next, the tooth profile data output unit 52 outputs the tooth profile data created in the process of S407 (S408).

Figure 22:
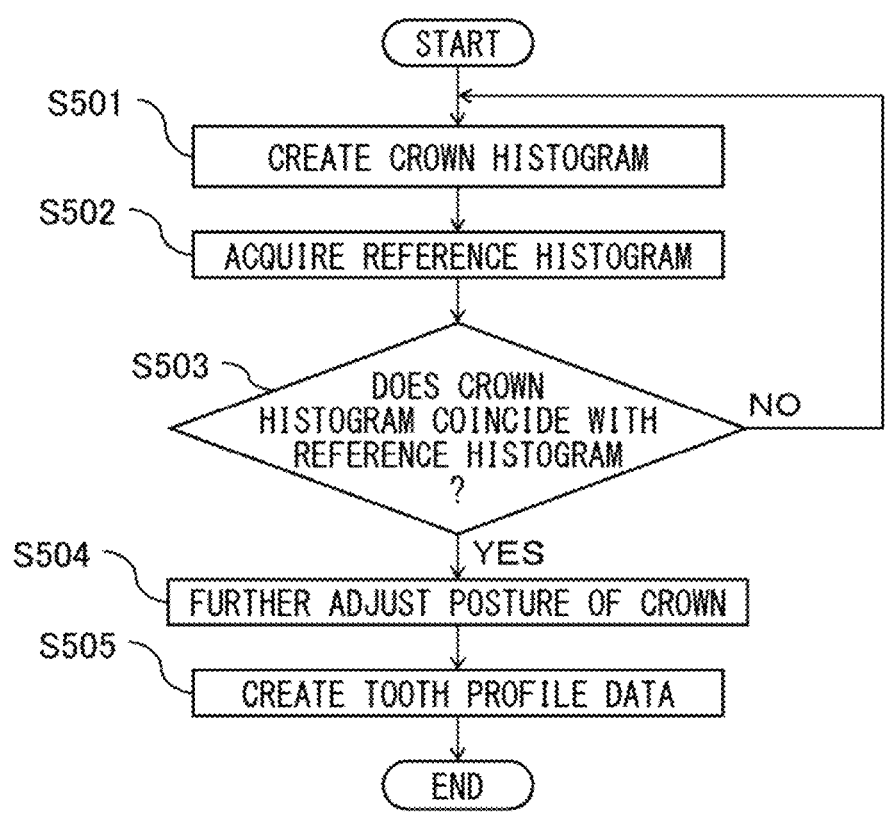
FIG. 22 is a flowchart illustrating more detailed process than the process of S407 illustrated in FIG. 21.

FIG. 22 is a flowchart illustrating more detailed process than the process of S407.

The processes of S501 to S504 are the same as the process of S301 to S304, and therefore a detailed explanation thereof will be omitted here.

The data creation unit 511 creates the tooth profile data by combining the crown data indicating the crown whose posture has been adjusted in the process of S504 and the reference data corresponding to the reference histogram judged to coincide with the crown histogram in the process of S503 (S505). In other words, the data creation unit 511 creates the tooth profile data indicating the tooth profile obtained by combining the crown corresponding to the crown data and a shape excluding a portion that coincides with the crown of a reference shape corresponding to the reference data. As an example, the data creation unit 511 may create the tooth profile data based on a method described in "Poisson Surface Reconstruction" Michael Kazhdan, Matthew Bolitho, Hugues Hoppe, Symposium on Geometry Processing 2006, 61-70. In this case, the data creation unit 511 creates a surface shape of the tooth from the normal vector of the vertex indicated by the crown data and the normal vector of the vertex indicated by the reference data. In other words, in the process of S505, the surface shape of the created waveform data (the second tooth profile data) is calculated based on the point group excluding a point group having normal vectors which is included in the first tooth profile data which is included within a predetermined distance or less from the point group included in the analysis target region, and the point group included in the analysis target region in the arrangement relationship calculated in the processes of S501 to S503, out of the point groups having normal vectors included in the first tooth profile data (the crown data indicating the crown whose posture has been adjusted in the process of S504).

Function and Effect of the Tooth Profile Data Creation Device According to the Embodiment The tooth profile data creation device 2 is capable of creating a crown model in which only the occlusal surface is changed by creating the tooth profile data from the crown corresponding to the crown data.

Modified Example of the Tooth Profile Data Creation Device According to the Embodiment The tooth profile data creation device 2 may estimate the tooth type within the analysis target region based on the distribution in the direction of the normal vector of the point groups having normal vectors included in the analysis target region of the inputted three-dimensional profile data. In this case, after the process of S405, a crown position information estimation unit estimates crown position information indicating the position of a tooth row of a tooth corresponding to the crown, from the distribution in the direction of the normal vector of each of the feature points converted to the local coordinate system in the process of S405. As an example, the position of the tooth row of a tooth corresponds to a number indicated by the notation of the FDI (Federation dentaire internationale) indicating the position of the tooth having the crown in the tooth row.

The crown position information estimation unit estimates the crown position information indicating the position of the crown from the distribution in the direction of the normal vector of each of the feature points by machine learning. In other words, when vector data of many numerical values is obtained and there is a pattern in the obtained vector data, the crown position information estimation unit learns the pattern, and estimates the number indicated by FDI notation based on the learned pattern.

The crown position information estimation unit which detects and specifies the feature points belonging to the crown portion of the number indicated by the FDI notation from the tooth type scan data is prepared by, for example, the following procedures (i) to (iii):

(i) From thousands of tooth type scan data, a two-dimensional histogram at a center position of the crown of the number indicated by FDI notation is acquired.

(ii) The crown position information estimation unit is caused to learn a correspondence between the number indicated by the FDI notation and the two-dimensional histogram.

(iii) It is confirmed whether the crown position information estimation unit that has learned the correspondence in procedure (ii) has a predetermined detection performance.

As an example, the crown position information estimation unit estimates the type of the tooth using the two-dimensional histogram shown in FIG. 18.

Next, the reference data acquisition unit 26 acquires the reference data corresponding to the estimated type of the tooth, as the first tooth profile data. The waveform data creation unit 51 calculates the arrangement relationship in which the error between the first tooth profile data and the point groups included in the analysis target region becomes minimum, by moving and/or rotating the first tooth profile data. Then, the waveform data creation unit 51 calculates the surface shape and creates the second tooth profile data based on the point groups having normal vectors included in the first tooth profile data and the point groups included in the analysis target region in the calculated arrangement relationship.

In this case, as based on the calculated arrangement relationship. described in the process of S505, the surface shape is calculated based on the point group excluding the point groups having normal vectors included in the first tooth profile data included within a predetermined distance or less from the point groups included in the analysis target region, and the point groups included in the analysis target region, out of the point groups having normal vectors included in the first tooth profile data based on the calculated arrangement relationship.

Although in the described embodiment, crown histograms are generated by moving or rotating the crown, and the generated crown histograms are compared with reference histogram, in an embodiment, a crown histogram is compared with reference histograms in which reference shape is moved or rotated. Further, in other embodiment, crown histograms in which the crown is moved or rotated are compared with reference histograms in which reference shape is moved or rotated.

All examples and conditional language provided herein are intended for pedagogical purposes of aiding the reader in understanding the invention and the concepts contributed by the inventor to furthering the art, and are to be construed as limitations to such specifically recited examples and conditions, nor does the organization of such examples in the specification relate to a illustrating of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a tooth direction estimation program that causes a computer to execute a process comprising:
   extracting a plurality of points from inputted three-dimensional profile data, the plurality of points indicating a surface of three-dimensional profile data;
   calculating an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of points; and
   specifying a direction of a tooth included in the region in accordance with the calculated arrangement relationship.

2. The tooth direction estimation program according to claim 1, wherein
   the calculating comprises:
   calculating each normal vector of the vertices included in the region; and
   estimating the arrangement relationship, based on a distribution of the calculated normal vectors, and a normal vector distribution of the vertices of the first profile.

3. The tooth direction estimation program according to claim 2, wherein the first profile includes shapes, whose shapes are different from each other.

4. The tooth direction estimation program according to claim 2, wherein
   the estimating comprises:
   creating a crown histogram indicating the distribution of the calculated normal vectors by moving and/or rotating the point group;
   acquiring a reference histogram indicating the normal vector distribution of the vertices in the first profile; and
   estimating the arrangement relationship based on crown posture information indicating a posture of the crown when the crown histogram and the reference histogram are judged to coincide.

5. The tooth direction estimation program according to claim 4, wherein
   the estimating further comprises:
   judging whether the crown histogram and the reference histogram coincide with each other; and
   further adjusting the posture of the crown when the crown histogram and the reference histogram are judged to coincide with each other, in order for the posture of the crown to coincide with the reference shape.

6. The tooth direction estimation program according to any one of claims 4, wherein the acquiring further comprises:
   acquiring a reference histogram when the reference shape is enlarged or shrunk.

7. The tooth direction estimation program according to claim 2, further comprising:
   extracting the vertices included in the crown corresponding to the acquired crown data; and
   the process for calculating each normal vector of the vertices further comprises
   calculating normal vectors of the extracted vertices.

8. The tooth direction estimation program according to claim 2, wherein
   the first profile is formed by polygons having triangular planes; and
   the direction of normal vectors of the extracted vertices is calculated by weighting the each direction of the normal vectors of the polygons including the vertex in accordance with an areas of the polygons.

9. The tooth direction estimation program according to claim 2, further comprising:
   defining a local coordinate axis, based on the distribution of direction of the calculated normal vectors of vertices, wherein
   the definition of the local coordinate axis further comprises:
   defining a first axis in a direction in which the calculated normal vector direction variance becomes maximum;
   defining a second axis calculating axis used for calculating the second axis in a direction in which the calculated normal vector direction variance becomes minimum;
   calculating the second axis from an outer product of the first axis and the second axis calculating axis; and
   defining a third axis in a direction orthogonal to both the first axis and the second axis.

10. A tooth axis direction estimation device, comprising:
    an extractor configured to extract a plurality of points from inputted three-dimensional profile data, the plurality of points indicating a surface of three-dimensional profile data;
    a calculator configured to calculate an arrangement relationship between a point group and a first three-dimensional profile data of a tooth in accordance with moving and/or rotating at least one of a first profile corresponding to the first three-dimensional profile data and the point group, the arrangement relationship corresponding to minimum difference between the point group and the three-dimensional profile data, the point group being included in a region of the extracted plurality of points; and
    a specifier configured to specify a direction of a tooth included in the region in accordance with the calculated arrangement relationship.

11. A tooth axis direction estimation method, comprising:
    extracting a plurality of points from inputted three-dimensional profile data, the plurality of points indicating a surface of three-dimensional profile data;
    calculating an arrangement relationship between a point group and a first three-dimensional profile data of a tooth in accordance with moving and/or rotating at least one of a first profile corresponding to the first three-dimensional profile data and the point group, the arrangement relationship corresponding to minimum difference between the point group and the three-dimensional profile data, the point group being included in a region of the extracted plurality of points; and
    specifying a direction of a tooth included in the region in accordance with the calculated arrangement relationship.

12. A non-transitory computer-readable recording medium having stored therein a creation program that causes a computer to execute a process comprising:

estimating a type of a tooth in an analysis target region, based on a normal vector direction distribution of point groups having normal vectors included in the analysis target region of inputted three-dimensional profile data;

calculating an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of point; and calculating a surface shape based on the point groups having normal vectors included in the first tooth profile data and the point groups included in the analysis target region based on the calculated arrangement relationship, and creating a second tooth profile data.

13. The creation program according to claim 12, wherein the surface shape is calculated based on the point group excluding the point groups having normal vectors included in the first tooth profile data included within a predetermined distance or less from the point groups included in the analysis target region, and the point groups included in the analysis target region in the calculated arrangement relationship.

14. A tooth profiled data creation device, comprising:

an estimator configured to estimate a type of a tooth in an analysis target region, based on a normal vector direction distribution of point groups having normal vectors included in the analysis target region of inputted three-dimensional profile data;

a first calculator configured to calculate an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of point; and a first calculator configured to calculate a surface shape based on the point groups having normal vectors included in the first tooth profile data and the point groups included in the analysis target region based on the calculated arrangement relationship, and creating a second tooth profile data.

15. A tooth profile data creation method, comprising:

estimating a type of a tooth in an analysis target region, based on a normal vector direction distribution of point groups having normal vectors included in the analysis target region of inputted three-dimensional profile data;

calculating an arrangement relationship between a point group and a first profile corresponding to a first three-dimensional profile data of a tooth in accordance with moving and/or rotating at least one of the first profile and the point group, the arrangement relationship corresponding to minimum difference between the point group and the first profile, the point group being included in a region of the extracted plurality of point; and calculating a surface shape based on the point groups having normal vectors included in the first tooth profile data and the point groups included in the analysis target region based on the calculated arrangement relationship, and creating a second tooth profile data.

* * * * *